(12) United States Patent
Windhorst et al.

(10) Patent No.: US 7,491,839 B2
(45) Date of Patent: Feb. 17, 2009

(54) PROCESSES FOR PREPARING ORGANIC COMPOUNDS HAVING IMPROVED COLOR CHARACTERISTICS

(75) Inventors: Kenneth Allen Windhorst, Portland, TX (US); Jennifer L. Bailey, Pampa, TX (US); Gabriel R. Chapa, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 666 days.

(21) Appl. No.: 10/635,983

(22) Filed: Aug. 7, 2003

(65) Prior Publication Data

US 2005/0033087 A1    Feb. 10, 2005

(51) Int. Cl.
*C07C 69/00*    (2006.01)
*C07C 53/00*    (2006.01)
(52) U.S. Cl. ...................... 560/129; 562/512
(58) Field of Classification Search ............... 560/191, 560/248; 562/593, 600, 608; 568/324, 340, 568/382, 410
See application file for complete search history.

(56) References Cited

U.S. PATENT DOCUMENTS

| | | | |
|---|---|---|---|
| 3,214,347 A * | 10/1965 | Grekel et al. .................. 203/63 |
| 3,293,292 A | 12/1966 | Oliver et al. ................. 260/533 |
| 3,887,595 A | 6/1975 | Nozaki ........................ 260/410 |
| 4,010,188 A | 3/1977 | Grasselli et al. .............. 260/465 |
| 4,268,689 A | 5/1981 | Knifton ....................... 560/263 |
| 4,487,720 A | 12/1984 | Fruchey ...................... 260/419 |
| 5,026,903 A | 6/1991 | Baker .......................... 560/232 |
| 5,091,587 A | 2/1992 | Drent .......................... 568/408 |
| 5,281,752 A | 1/1994 | Fujiwara et al. ............. 562/522 |
| 6,211,405 B1 | 4/2001 | Cheung et al. .............. 562/519 |

* cited by examiner

*Primary Examiner*—Karl J Puttlitz
(74) *Attorney, Agent, or Firm*—M. Susan Spiering

(57) ABSTRACT

Carboxylic acids, ketones, and esters having improved color characteristics are produced by combining small quantities of water with these compounds. An amount of water ranging from about 100 ppm to about 50,000 ppm of the organic compound is combined to provide lighter color compounds in comparison to these same compounds to which no water is added. Additionally, the color characteristics of the organic compounds may be improved by introducing a stream of the organic compound into at least one distillation column maintained at a temperature of about 23° C. to about 250° C. and at a pressure of about 10.1 kPa to about 202.6 kPa. Subjecting the organic compound stream to distillation under these conditions allows precursors of color bodies, having boiling points lower than the boiling point of the product being produced, to thermally breakdown or to be removed in the overhead stream form the distillation column.

16 Claims, 1 Drawing Sheet

US 7,491,839 B2

PROCESSES FOR PREPARING ORGANIC COMPOUNDS HAVING IMPROVED COLOR CHARACTERISTICS

FIELD OF THE DISCLOSURE

Figure 1:
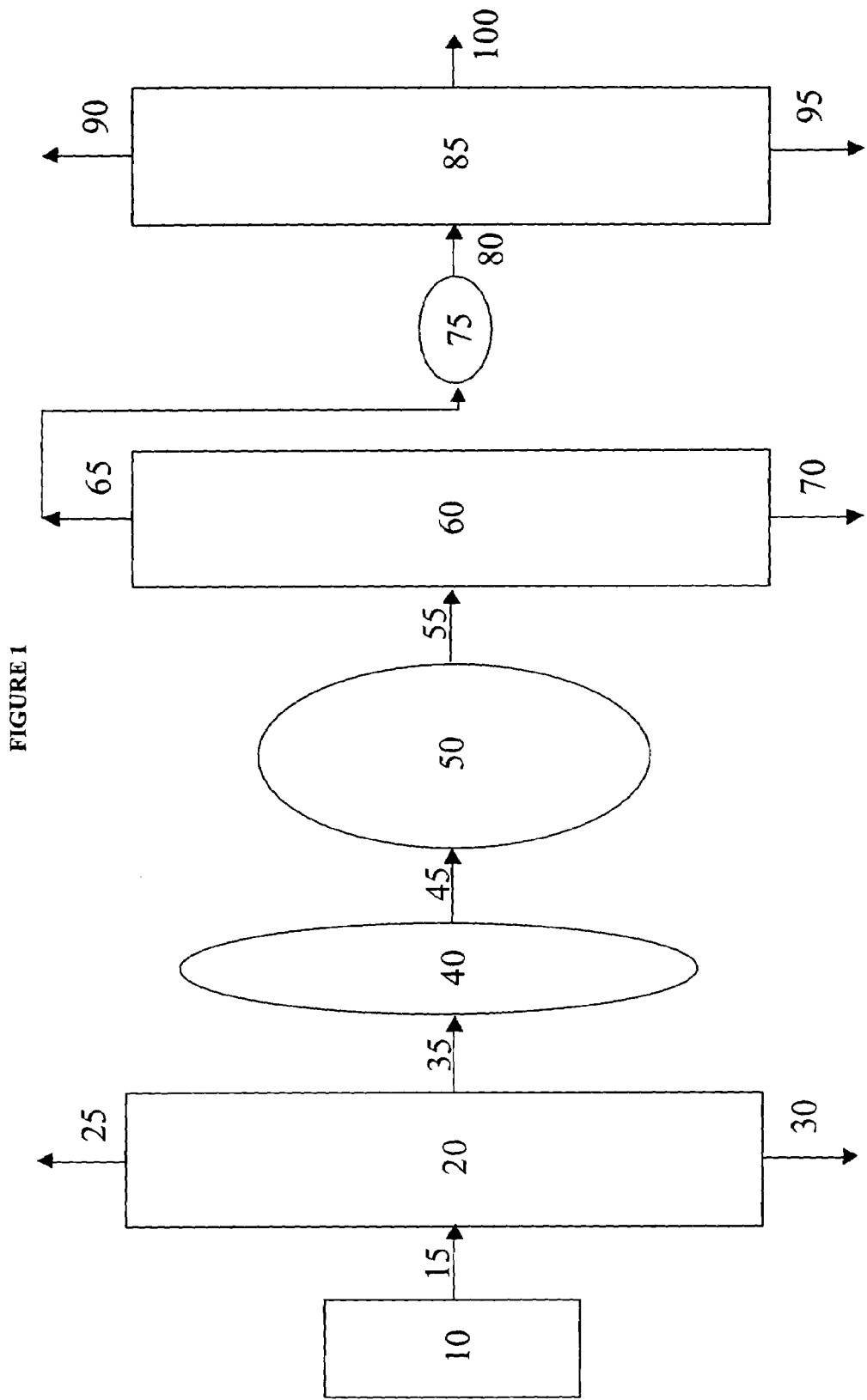

This disclosure relates to processes for preparing carboxylic acids, ketones, and esters having improved color characteristics.

BACKGROUND INFORMATION

There are numerous known processes for producing carboxylic acids, ketones, and esters. For example, U.S. Pat. Nos. 3,887,595, and 6,211,405 disclose processes for producing carboxylic acids by carbonylating olefinically unsaturated compounds such as alcohols, ethers, and esters. U.S. Pat. No. 5,281,752 discloses a process for producing lower carboxylic acids by reacting alkanes with carbon dioxide. U.S. Pat. No. 5,091,587 discloses a process for the preparation of ketones which comprises reacting a conjugated diolefin and water in the liquid phase in the presence of a catalyst system comprising: a group VIII metal compound and a source of protons. U.S. Pat. No. 4,010,188 discloses a process for the oxidation of saturated hydrocarbons in the presence of a catalyst to produce acids. U.S. Pat. No. 3,293,292 discloses a liquid phase oxidation of butane in the presence of a cobalt containing catalyst system to produce carboxylic acids. U.S. Pat. No. 4,487,720 discloses a process of the production of acids by oxidizing saturated aliphatic aldehydes in the presence of catalyst systems. U.S. Pat. No. 5,026,903 discloses a process for producing of glycol esters such ethylidene diacetate by the reaction of mixtures of dimethyl acetal, methyl acetate and carbon monoxide. The catalyst system charged to the reactor contains rhodium atoms, lithium iodide and optionally an organic ligand. U.S. Pat. No. 4,268,689 also discloses a process for the production of glycol esters.

A problem associated with carboxylic acids, ketones, and esters production and storage is color quality. To use carboxylic acids and other organic compounds for certain applications, the compounds must exhibit a light color. Generally speaking, the darker color values for these organic compounds do not affect the functionality of the compounds for most applications. However, most purchasers of these organic compounds believe that "water white" compounds are of higher quality than compounds possessing higher color properties and demand water white organic compounds. Typically, compounds exhibiting an APHA color (Pt—Co) of 15 or less are considered to be of water white quality. If the compounds are not of a water white quality, expensive purification schemes must be undertaken to purify the product to achieve acceptable color characteristics. For example, expensive and multiple hydrogenation and acid treatment processes may be necessary to achieve a compound having water white characteristics.

BRIEF DESCRIPTION OF DISCLOSURE

This disclosure relates to processes for preparing certain organic compounds such as carboxylic acids, ketones, and esters having low color characteristics. A first embodiment involves combining water with the organic compound at a concentration of 100 ppm to 50,000 ppm water. A second embodiment involves removing a product stream containing the organic compound from a reaction system in which the organic compound is prepared and introducing the product stream into a distillation column having a lower portion and an upper portion wherein the upper and lower portions are maintained at a temperature of from about 23° C. to about 250° C. and at a pressure of about 10.1 kPa to about 202.6 kPa. Subjecting the product stream to distillation under these conditions thermally breaks down, or removes, precursors of color bodies, having boiling points lower than the boiling point of the product being produced.

A third embodiment includes combining the process of the first two embodiments by producing a product that has been subjected to isolation and purification in a system including a distillation column operating at the temperatures and pressures described above and combining water with the organic compounds as described above.

These processes may be implemented to prepare carboxylic acid, ketone, and glycol ester products having stable APHA color values of 15 or less. Having a stable APHA color of 15 or less means that the products will exhibit a color value within this range after being boiled for at least one hour at one atmosphere (101.3 kPa) pressure.

DRAWING

FIG. 1 is a schematic diagram of an embodiment of the process of this invention.

DETAILED DISCLOSURE

This disclosure relates to processes for preparing certain carboxylic acids, ketones, and esters having low color properties. The organic compounds include $C_1$ to $C_6$ carboxylic acids, ketones having boiling points from 54° C. to 170° C., and esters having boiling points from about 168° C. to about 250° C. These various organic compounds may be the reaction product of a variety of processes for producing these compounds. For example, carboxylic acids are often commercially prepared by carbonylation of alcohols, esters, or ethers to produce the corresponding carboxylic acid. A widely used commercial carbonylation process is the production of acetic acid from carbonylation of methanol. Of course, the carbonylation process is applicable to the carbonylation of higher homologues of methanol to form acids that are the higher homologues of acetic acid. The carboxylic acids useful in the preparation process described in this disclosure may be the reaction product of other processes such as oxidizing corresponding aldehydes, alkanes, and alkenes.

Additionally, the processes described here may also be used to prepare low color value carboxylic acids that are prepared by reacting alkanes with carbon monoxide in the presence of palladium and/or copper catalysts and salts of peroxy acids. The carboxylic acids may also be produced thorough the oxidation of saturated alkanes. For example, this oxidation process may be used to produce butyric acid through the oxidation of butane.

In summary, the $C_1$ to $C_6$ carboxylic acids produced by any process, including but not limited to the exemplary processes referred to in the BACKGROUND INFORMATION above, may exhibit improved color properties as a result of the color improvement processes described in this disclosure.

Any process, including but not limited to the exemplary processes referred to in the BACKGROUND INFORMATION above, may also produce the ketones and esters that exhibit improved color characteristics as a result of the processes described herein.

An exemplary process scheme for the production of carboxylic acids is depicted in FIG 1. Specifically, the process depicted in FIG. 1 is for the production of butyric acid through the oxidation of butane. It is understood that the process scheme depicted may be used to produce a variety of other carboxylic acids, including, but not limited to, acetic acid, through the oxidation of naptha, pentane, and other feedstocks. A liquid phase reactor 10 is charged with air or oxygen content enriched air. The oxygen content of the feed may be at any level, including pure oxygen. Of course, when using pure oxygen or highly enriched air, appropriate safety precautions should be observed to prevent fire or explosion hazards. However, in terms of a balance of reaction efficiency and economics, generally an enriched air feed having an oxygen content from about 20% to about 30% is found to be useful. The reactor 10 is also charged with pure butane although a stream contain less than pure butane may be used provided the process scheme used can accommodate removal of any impurities included with the butane.

The butane is oxidized in the presence of any suitable oxidation catalyst. An exemplary catalyst is cobalt salt catalyst present at a concentration of less than 5,000 ppm. Additionally, recycle steams as described hereinafter, may be routed to the reactor. As the reaction proceeds, the reactor should be maintained at temperature from about 100° C. to about 200° C. and a pressure from about 6.20 Pa to about 6.89 Pa. If the feed is naptha, the pressure should be maintained form about 3.44 Pa to about 5.51 Pa. A crude product stream 15 is withdrawn as a sidestream 15 from the reaction zone and introduced into a first distillation column 20 maintained at a bottom portion temperature ranging up to about 200° C. and a top portion temperature ranging from about 100° C. to about 120° C. and a pressure of about 10.13 kPa to about 101.3 kPa to separate an overhead light ends stream 25 and a heavy ends cut 30. The light ends stream 25 containing alcohols is recycled to the reactor 10 and the heavy ends cut 30 is primarily waste product and may be disposed of by any suitable means, including burning. A product stream 35 is withdrawn as sidestream 35, which is introduced into a first treatment unit 40. The treatment taking place in unit 40 may be any suitable hydrogenation treatment to improve the properties of the product stream 35. A treated product stream 45 is withdrawn form treatment unit 40 and introduced into a second treatment unit 50 which may be any suitable treatment step to remove impurities in the product stream, such as 3-hydroxy 2-butanone. Suitable treatment methods are nitric acid oxidation treatment processes that are well known, such as referred in U.S. Pat. No. 6,590,129. A treated product stream 55 is then withdrawn from treatment unit 50 and introduced into a second distillation column 60 maintained at a bottom portion temperature of from about 100° C. to 200° C. and a pressure of 10.13 kPa to 101.3 kPa. A heavy ends cut 70 containing primarily gamma butyrolactone and crotonic acid is removed from the bottom of the second distillation column 60. The heavy ends cut may be recycled to the reactor 10. An overhead product stream 65 is taken from the second distillation column 60. The overhead contains primarily propionic acid and acetic acid and is recycled to reactor 10. The product stream 65 is routed to a third treatment unit 55. The product stream 65 is heated in the third treatment step. In one embodiment, the heat treatment involves boiling the product stream for an average residence time of one hour at atmospheric pressure. The boiling point for the product stream is approximately 165° C. The heat treatment step will have the effect of accelerating adverse color producing reactions that might occur upon normal aging of the product. The heat treatment step may also remove certain impurities through cracking or polymerization mechanisms. A treated stream 80 is withdrawn from the third treatment unit 75 and introduced into a third distillation column 85 maintained at a bottom portion temperature of up to 200° C. and a top portion temperature of up to 150° C. and a pressure of 10.13 kPa to 101.3 kPa to separate the butyric acid product from remaining light ends 90 and heavy ends 95 as the product is withdrawn as sidestream 100 from the third distillation column. Optionally, the product butyric acid stream may be cooled.

As mentioned previously, it is desirable for many purchasers and applications that the butyric acid, ketones, and esters described herein have low color values. An established method for determining the color of light colored liquids such as these organic compounds is to determine the APHA number or the liquid. The lower the APHA color value, the more colorless the liquid. The procedure for determining APHA color number is set forth in ASTM D1209-62T and E 202-62T. With respect to $C_1$ to $C_6$ carboxylic acids, low color values means acids having stable APHA colors of less than or equal to 15. For ketones, low color refers to stable APHA color values of less than or equal to 15 and for esters, low color refers to stable APHA values of less than or equal to 15.

In the butyric production process depicted in FIG. 1, typical finished product APHA color values may range from about 0 to about 5. But, the color values of the product often increase over time as the product ages under typical storage conditions. Often the color degradation is intensified upon exposure of the organic compounds to heat.

To provide a product having desirable low color values, it may be necessary to undertake expensive and time consuming additional purification steps to produce a low APHA color value products. It has been unexpectedly determined that stable low APHA color value carboxylic acid, ketone, and glycol ester products may be consistently produced without the need for additional expensive and time consuming purification steps. The low color value products may be produced through each of the two different processes described in this disclosure and through the use of a combination of the two processes.

In a first embodiment, the stable color values of the organic compounds are improved by combining a small amount of water with the product organic compounds. In one embodiment, the water is added directly to the finished organic compound product under conditions of agitation, such as stirring. In another embodiment, the water may be conveniently added by simply adding the water to an empty mixing vessel and then adding the organic compound to the vessel. The addition of the organic compound will typically provide sufficient mixing energy to form a mixed solution having a consistent concentration of water. The water may be added to the organic compounds over a wide range of temperatures. For example, the water and the organic compounds may be combined at any temperature the water and the organic compound are in liquid phases. In general, when the organic compound is butyric acid, in one embodiment, the water and butyric acid may be combined at a temperature of from about 0° C. to about 160° C., depending on the pressure of the system in which combining the water and butyric takes place. In one embodiment, the water and butyric acid are combined at a temperature of about 20° C. to about 50° C.

In one process, the water is combined with the $C_1$ to $C_6$ carboxylic acids, ketones having boiling points from 54° C. to 170° C., and esters having boiling points from about 168° C. to about 250° C. until a concentration of about 100 ppm water to about 50,000 ppm water is achieved. In another embodiment, water is combined with a butyric acid product to provide a water concentration of about 100 ppm to about 10,000 ppm. In still another embodiment, water is combined with butyric acid to achieve a concentration of about 500 ppm water to about 1000 ppm water.

As mentioned, the water may be combined with the organic compounds under conditions of agitation to achieve uniform distribution of the water throughout the organic compound product to provide a more uniform concentration of the water throughout the organic compound.

Alternatively, water may be added to the organic compound products by adding water in an overhead cut product stream of any conventional production process for producing the organic compounds. For example, with reference to FIG. 1, water may be added to overhead stream 65 to achieve the beneficial color characteristics described in this disclosure.

EXAMPLES

The following Examples demonstrate the color characteristics improvement benefits resulting from adding water to a butyric acid product.

Example 1

A commercially produced butyric acid was found to have an APHA color value of 4. A first sample of the butyric acid was boiled for one hour and found to have an APHA color of 31 after boiling. Water was added to a second sample of the same commercially produced batch of butyric acid, while stirring at room temperature, until a concentration level of 1000 ppm water was reached. The water containing second sample was then boiled for one hour in the same manner as the first sample. Following boiling, the APHA color value of the second sample was determined to be 12.

Examples 2-4

The effect of color degradation through aging was determined on three samples from a commercially produced butyric acid run. The samples were prepared by successive distillations of the same portion of the commercially produced butyric acid run. The APHA colors of the samples were determined to be as follows:

Example 2 8

Example 3 4

Example 4 4

The color variance of the samples is attributable to the fact that more color bodies were present in the first distillation sample as compared to the second and third distillation samples.

Each sample was allowed to stand at room temperature undisturbed for 24 hours and the APHA colors of the samples were determined as follows:

Example 2 20

Example 3 2

Example 4 9

Examples 5-7

The effect of color improvement though the addition of water was determined on three samples from a commercially produced butyric acid run. The samples were prepared by successive distillations of the same portion of the commercially produced butyric acid run. The APHA colors of the samples were determined to be as follows:

Example 5 13

Example 6 3

Example 7 1

The color variance of the samples is attributable to the fact that more color bodies were present in the first distillation sample as compared to the second and third distillation samples.

To each of these samples was added 20,000 ppm, water while stirring at room temperature, to ensure uniform distribution of the water. Following addition of the water, the APHA colors of the samples were determined as follows:

Example 5 1

Example 6 1

Example 7 1

A second process by which the color of $C_1$ to $C_6$ carboxylic acids, ketones having boiling points from 100° C. to 170° C., and esters having boiling points from about 168° C. to about 250° C. may be improved is the use of high temperature conditions during the separation and purification of product streams of these organic compounds. It has been determined that introducing a product stream of the organic compound into a distillation column having a lower portion and an upper portion wherein the upper and lower portions are maintained at a temperature of about 23° C. to about 250° C. and at a pressure of about 10.1 kPa to about 202.6 kPa such that precursors of color bodies having boiling points lower than the boiling point of the product being produced may thermally broken down or removed in the overhead of the distillation column. The stream may be introduced into one or more distillation columns operating under these outlined conditions.

An exemplary embodiment is seen by reference to FIG. 1. Color improvement of the butyric acid product may be achieved by operating the first distillation column 20, the second distillation column 60, or the third distillation column 85 the upper and lower portions at a temperature of about 23° C. to about 250° C. and at a pressure of about 10.1 kPa to about 202.6 kPa. Subjecting the product stream to distillation under these conditions allows precursors of color bodies, having boiling points lower than the boiling point of the product being produced, to be removed in the overhead stream from the distillation column.

In another embodiment, one of the distillation columns may be operated at upper portion and lower portion temperatures of 170° C. to about 180° C. and at pressures of about 101 kPa to about 202 kPa to improve color characteristics of the butyric acid. Alternatively, all three or any two of the distillation columns may be operated at the above-stated conditions to achieve color improvement.

In addition to using the water addition process for color improvement outlined above alone or the high distillation column temperature process discussed above in isolation, the improved color characteristics may be obtained by using the water addition and high distillation temperature processes in combination with each other. An additional benefit of using the heat treatment step is the removal of low boiling impurities.

Without being bound by theory, it is believed that the processes disclosed herein obtain improved color properties of the organic compound products through thermally breaking down, removing, or preventing the formation of certain color bodies, or precursors to the color bodies, during the processes for producing the organic compounds of interest. Specifically, it is believed that color degradation derives from the formation of Michael Adducts during the production of the organic compounds in accordance with this description.

It is believed that a compound formed from an unsaturated ketone and a carboxylic acid in the production of the relevant organic compounds leads to formation of a Michael Adduct in accordance with the following reaction process:

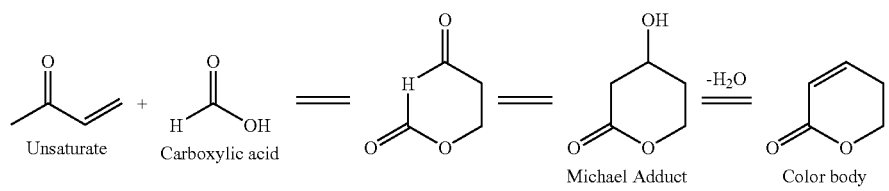

As seen from this reaction process, the Michael adduct, upon dehydration, yields color bodies thought to lead to the undesirable darker color products. It is believed that by adding water to the organic compound products, formation of the color bodies is prevented. With respect to the second process involving operating the distillation column or columns during recovery of the organic compounds at the described temperatures and pressures, a different mechanism, accounts for color improvement in the organic compounds produced. In this process, the intermediate product that is a precursor of the Michael Adduct may be broken down thermally, thereby preventing the ultimate formation of the offensive color bodies in the organic compound products. Alternatively, the color precursor may be removed in the overhead of the distillation column as long as the precursor boils at a lower temperature than the desired product organic compound.

All patents and publications referred to herein are hereby incorporated by reference in their entireties.

Although the present invention and its advantages have been described in detail, it should be understood that various changes, substitutions, and alterations could be made without departing from the spirit and scope of the invention as defined by the following claims.

What is claimed is:

1. A process for preparation of a color stable organic compound/water mixture from an organic compound selected from the group consisting of $C_1$ to $C_6$ carboxylic acids, ketones having boiling points from 154° C. to 170° C., and esters having boiling points from about 168° C. to about 250° C., the process comprising combining the organic compound with water under conditions of agitation to form a mixed solution of the organic compound and water having a consistent concentration of water comprising from about 100 ppm to about 50,000 ppm water to produce the color stable organic compound/water mixture, wherein the color stable organic compound/water mixture has an APHA color value of 15 or less after being boiled for at least one hour at one atmosphere of pressure.

2. The process of claim 1 wherein the water and the organic compound are combined to produce the color stable organic compound/water mixture at a temperature of about 0° C. to about 160° C.

3. The process of claim 2 wherein the conditions of agitation include stirring.

4. The process of claim 3 wherein the color stable organic compound/water mixture has an APHA color value of 12 or less after being boiled for at least one hour at one atmosphere of pressure.

5. The process of claim 4 wherein the organic compound is a $C_1$ to $C_6$ carboxylic acid.

6. The process of claim 5 wherein the organic compound is butyric acid.

7. The process of claim 6 wherein the color stable organic compound/water mixture comprises from 100 ppm to about 10,000 ppm water.

8. The process of claim 7 wherein the water and the organic compound are combined to produce the color stable organic compound/water mixture product at a temperature of about 20° C. to about 50° C.

9. The process of claim 8 wherein the color stable organic compound/water mixture comprises from 500 ppm to about 1,000 ppm water.

10. A process for preparation of a color stable organic compound/water mixture, wherein the organic compound is selected from the group consisting of $C_1$ to $C_6$ carboxylic acids, ketones having boiling points from 154° C. to 170° C., and esters having boiling points from about 168° C. to about 250° C., the process comprising:
(a) removing a crude product stream comprising the organic compound from a reaction zone in which the organic compound is prepared;
(b) introducing the crude product stream into a distillation column having a lower portion and an upper portion wherein the upper portion and the lower portion are maintained at a temperature of about 23° C. to about 250° C. and at a pressure of about 10.1 kPa to about 202.6 kPa;
(c) removing the organic compound as a side-stream from the distillation column to produce a finished organic compound; and
(d) combining the finished organic compound with water under conditions of agitation to form a mixed solution of the organic compound and water having a consistent concentration of water comprising from about 100 ppm to about 50,000 ppm water to produce the color stable organic compound product, wherein the color stable organic compound/water mixture has an APHA color value of 15 or less after being boiled for at least one hour at one atmosphere of pressure.

11. The process of claim 10 wherein the water and the organic compound are combined to produce the color stable organic compound/water mixture at a temperature of about 0° C. to about 160° C.

12. The process of claim 11 wherein the conditions of agitation include stirring.

13. The process of claim 12 wherein the organic compound is a $C_1$ to $C_6$ carboxylic acid.

14. The process of claim 13 wherein the organic compound is butyric acid.

15. The process of claim 14 wherein the water and the butyric acid are combined at a temperature of about 20° C. to about 50° C. and the color stable organic compound/water mixture comprises from 100 ppm to about 10,000 ppm water.

16. The process of claim 15 wherein the color stable organic compound/water mixture comprises from 500 ppm to about 1,000 ppm water.

* * * * *